United States Patent [19]
Andre et al.
[11] Patent Number: 4,675,419
[45] Date of Patent: Jun. 23, 1987

[54] PROCESS FOR PREPARING α-HYDROXY-ACIDS AND COMPOUNDS OBTAINED BY THIS PROCESS

[75] Inventors: Jean-Daniel Andre, Sisteron; Pierre-Jean Grossi, Aramon; Alain Heymes, Sisteron, all of France; Giovanni V. Manzaroli, Milan, Italy
[73] Assignee: Sanofi, Paris, France

[21] Appl. No.: 800,229
[22] Filed: Nov. 21, 1985
[30] Foreign Application Priority Data
Nov. 29, 1984 [FR] France ................................ 84 18202
[51] Int. Cl.[4] ..................... C07C 51/42; C07D 333/24
[52] U.S. Cl. ...................................... 549/79; 562/421; 549/473; 549/469; 549/32; 548/562; 548/502
[58] Field of Search ................... 549/79, 473, 469, 32; 562/421; 548/502, 562

[56] References Cited

U.S. PATENT DOCUMENTS

| | | | |
|---|---|---|---|
| 4,219,659 | 8/1980 | Fujisawa | 549/79 |
| 4,266,067 | 5/1981 | Fujisawa | 549/79 |

OTHER PUBLICATIONS

Hilgerag Preparative Org. Chem. 1972, p. 341.

*Primary Examiner*—Nicky Chan
*Attorney, Agent, or Firm*—Bacon & Thomas

[57] ABSTRACT

The invention relates to a process for preparing α-hydroxy-acids of general formula:

$$Cy-\underset{R}{\overset{OH}{C}}-CO_2H$$

in which R represents hydrogen or a lower alkyl radical and Cy represents a phenyl, naphthyl or heterocyclic radical, these latter three radicals optionally comprising one or more substituents selected from the group consisting of lower alkyl, lower alkenyl, lower alkynyl, lower alkoxy radicals and halogen atoms, process which comprises the treatment of an α-monohalogenated ketone of general formula:

$$Cy-\overset{O}{\overset{\|}{C}}-\underset{R}{CH}-X$$

in which R and Cy have the same meaning as above and X represents chlorine, bromine or iodine, in the presence of an aqueous solution of an alkali metal hydroxide, a non-polar organic solvent selected from an aromatic or alicyclic hydrocarbon and oxygen in excess optionally in the presence of an inert gas, the treatment being carried out at a temperature ranging from the boiling temperature of the reaction medium at atmospheric pressure and 240° C. under pressure and the alkali metal so formed is then acidified to obtain the desired acid.

18 Claims, No Drawings

PROCESS FOR PREPARING α-HYDROXY-ACIDS AND COMPOUNDS OBTAINED BY THIS PROCESS

This invention relates to a novel process for preparing α-hydroxy-acids and to the compounds obtained by this process.

More particularly, the invention concerns a novel process for preparing α-hydroxy-acids of general formula:

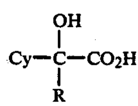

in which R represents hydrogen or a lower alkyl radical and Cy represents a phenyl, naphthyl or a heterocyclic radical, these latter three radicals optionally comprising one or more substituents selected from the group consisting of lower alkyl, lower alkenyl, lower alkynyl, lower alkoxy radicals and halogen atoms such as chlorine or bromine.

In the present context, the terms cited hereunder have the following meaning:

"lower alkyl" designates saturated aliphatic hydrocarbon radicals having up to 4 carbon atoms, such as methyl, ethyl, n-propyl, isopropyl, n-butyl, isobutyl or tert-butyl;

"lower alkenyl" designates unsaturated aliphatic hydrocarbon radicals comprising one or two double bonds and having from 2 to 4 carbon atoms such as vinyl, allyl or butenyl;

"lower alkynyl" means unsaturated aliphatic hydrocarbon radicals comprising one or two triple bonds and having from 2 to 4 carbon atoms such as ethynyl, propargyl or butynyl;

"lower alkoxy" designates the hydroxyl group substituted by a lower alkyl radical as described hereabove;

"heterocyclic radical" designates more particularly a furyl, thienyl, pyrrolyl, benzofuryl, benzothienyl or indolyl radical.

Thus, taking the above-cited meanings into account, the Cy radical can more particularly represent an isobutyl-phenyl, preferably 4-isobutylphenyl, a methoxynaphthyl preferably 6-methoxy-2-naphthyl, a 5-chloro- or 5-bromo-6-methoxy-2-naphthyl or a thienyl preferably a 2-thienyl radical.

These compounds are particularly useful as intermediates in the synthesis of alkanoic acids of general formula:

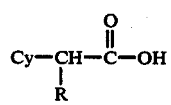

in which R and Cy have the same meaning as above.

Amongst these compounds, which are especially known as anti-inflammatory, antipyretic or antalgic agents the following may be cited: 2-(4-isobutyl-phenyl)-acetic acid or ibufenac, 2-(4-isobutyl-phenyl)-propionic acid or ibuprofen, 2-(4-isobutyl-phenyl)-butyric acid or butibufen, 2-(6-methoxy-2-naphthyl)-propionic acid or naproxen or again 2-(2-thienyl)-propionic acid.

The synthesis of ibuprofen from 2-(4-isobutyl-phenyl)-2-hydroxy-propionic acid as well as the preparation of this latter intermediate compound has been described in Japanese Patent Application No. 54-39042 (C.A. 91, P140574u).

Following the process so described, the α-hydroxy-acid in question is prepared from ethyl 2-(4-isobutyl-phenyl)-2-oxo-acetate by reaction with a methyl magnesium halide in ether followed by alkaline hydrolysis in accordance with the conditions of the GRIGNARD reaction.

Though the yields obtained are considerable, the working conditions of such a reaction are expensive and difficult to carry out on the industrial scale (use of magnesium, anhydrous reaction medium etc . . . ).

Other publications also report processes of preparation of α-hydroxy-alkanoic acids of formula (I').

In most cases, these processes present disadvantages which preclude their use on the industrial scale.

These disadvantages can for instance be due to the use of starting products which are relatively difficult to obtain.

However, a process of preparation of certain α-hydroxy-phenylalkanoic acids is known involving working conditions which can be extrapolated without any major difficulty on the industrial scale.

This process, which is described in J.A.C.S. 72, 1642–1644 (1950) or in Org. Synth. III, 538–541(1955) is based on a transposition reaction of α,α-dihalogenated phenylalkyl ketones involving the use of aqueous sodium hydroxide.

Attempts have been made to prepare acids of formula I and in particular 2-(4-isobutyl-phenyl)-2-hydroxy-propionic acid following such a method but with little succes.

The highest yields obtained in the desired acid were only about 19%, 4-isobutyl-benzoic acid being the product most frequently synthetized. In consequence, the preparation of α-hydroxy-phenylalkanoic acids of formula I following a process which can be used in industry remains of paramount importance.

It has now been found, in accordance with the invention, that the α-hydroxy-acids of formula I can be prepared on the industrial scale by means of a transposition reaction of an α-monohalogenated ketone and not of an α,α-dihalogenated ketone using oxygen, an alkali metal hydroxide in aqueous solution and a non-polar organic solvent.

Thus, the process of the invention for the preparation of the α-hydroxy-alkanoic acids in question consists in:

treating an α-monohalogenated ketone of general formula:

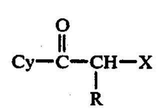

in which R and Cy have the same meaning as above and X represents chlorine, bromine or iodine, in the presence of an aqueous solution of an alkali metal hydroxide such as lithium, sodium or potassium hydroxide, a non-polar organic solvent selected from an aromatic or alicyclic hydrocarbon and oxygen in excess optionally in the presence of an inert gas forming a mixture such as air, treatment being carried out at a temperature ranging from the boiling temperature of the reaction medium at atmospheric pressure to 240° C. under pressure, then acidifying the alkali metal salt so formed to obtain the desired acid.

In the particular case of 2-(4-isobutyl-phenyl)-2-hydroxy-propionic acid, yields of 70 to 90% can be obtained by the process of the invention with less benzoic acid derivatives being produced by a side-reaction.

As aromatic hydrocarbon, toluene, xylenes, isobutylbenzene or naphthalene can be used and, as alicyclic hydrocarbon, cyclohexane can, for instance, be employed. Generally xylenes are preferred and in particular industrial xylene for reasons of economy.

It has been observed that the presence of oxygen in at least a stoechiometric amount is absolutely necessary in the reaction medium for the production of compounds of formula I with high yields.

Under inert atmosphere, yields in α-hydroxy-acids of formula I, for example 2-(4-isobutyl-phenyl)-2-hydroxy-propionic acid, are, in fact, practically nil.

Where the α-monohalogenated ketones of formula II are used at the boiling temperature of the reaction medium under atmospheric pressure either pure oxygen or oxygen accompanied by an inert gas can be utilized.

However, at higher temperatures, for instance at temperatures in the region of 200° C., oxygen accompanied by an inert gas is preferably used.

At atmospheric pressure and at the boiling temperature of the reaction medium, the transposition reaction is performed in 20 to 25 hours providing yields of at least 70%.

The non-limitative working conditions given below are usually utilized in the presence of oxygen in excess or air in excess:

0.5 to 40 parts by weight of alkali metal hydroxide
5 to 400 parts by volume of water
2 to 40 parts by volume of organic solvent these proportions being used for 1 part by weight of ketone of formula II, the reaction being carried out at the boiling temperature of the mixture so formed.

It has been found, in particular, that the transposition reaction of the invention can be considerably accelerated by increasing the temperature.

It has, in fact, been observed that an increase in the reaction temperature, preferably to between 160° and 240° C., which necessitates operating under pressure, produces the same effect as an increase in the duration of the reaction.

Thus, at a temperature ranging from 180° to 220° C., the transposition reaction in the reaction medium maintained under stirring and pressure, for instance by using a bomb-apparatus, can be performed in minutes for instance in 15 to 60 minutes.

At those temperatures between the boiling temperature of the reaction medium at atmospheric pressure and 240° C. under pressure, the following nonlimitative working conditions are generally used:

0.5 to 10 parts by weight of an alkali metal hydroxide
5 to 150 parts by volume of water
1 to 30 parts by volume or organic solvent these proportions being used for 1 part by weight of ketone of formula II.

In accordance with a first manner of applying the process of the invention at a temperature between the boiling temperature of the reaction medium at atmospheric pressure and 240° C. under pressure, the alkali metal hydroxide in solution, xylene and monohalogenated ketone of formula II are mixed in the bomb-apparatus which is then closed and heated to the desired temperature while oxygen under pressure, optionally mixed with an inert gas, is applied, generally at a pressure of about 20 bars.

A second mode of operation can also be used which consists in:

first introducing into the bomb-apparatus the aqueous solution of alkali metal hydroxide as well as the xylene if the monohalogenated ketone of formula II is liquid, heating the bomb-apparatus when closed to obtain the desired temperature, introducing the oxygen or the oxygen mixed with an inert gas and finally, using a dispensing pump, introducing the monohalogenated ketone of formula II as such or dissolved in xylene.

Generally, the introduction of the monohalogenated ketone is performed in about 2 hours.

The yield in α-hydroxy-acid of formula I can be considerably increased, using the above working conditions, by adding the monohalogenated ketone in a continuous operation.

The separation and purification of the α-hydroxy-acids of formula I can be obtained by precipitating the metal salts thereof from the reaction medium and then acidifying. Using these operating conditions, the acidification of the total mixture containing the base in excess can be avoided together with the extraction of the α-hydroxy-acids in question from a considerable volume of water.

Moreover, when the metal salts of the α-hydroxy-acids are precipitated the other acid impurities together with the sodium halides formed are not included in the precipitate but remain, owing to their greater solubility, almost entirely in the reaction medium and in the water.

These α-hydroxy-acid salts can therefore be removed by filtration.

This constitutes an undeniable advantage as the subsequent reactions, leading to the alkanoic acids of formula (I'), produce no or very few impurities.

These alkanoic acids in pure form can thus be obtained by a simple operation of purification of the starting-products namely the α-hydroxy-alkanoic acids of formula I.

In contrast with this, other prior processes only enable purification to be carried out at the level of the alkanoic acid, an operation which has been found to be difficult at this stage.

Another advantage of the process of the invention lies in the fact of being able to use starting compounds which are particularly valuable because very easily produced i.e. the compounds of formula II.

These compounds of formula II can be obtained, for instance, from a compound of general formula:

$$\text{Cy—H} \qquad \text{III}$$

in which Cy has the same meaning as above, by acylation, in accordance with the conditions of the FRIEDEL-CRAFTS reaction, by means of the α-monohalogenated acyl halides of general formula:

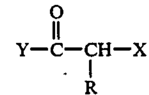

IV in which R and X have the same meaning as above, and Y represents chlorine or bromine, or by means of anhydrides or other equivalent derivatives of the above compounds of formula IV.

Other procedures can be used to obtain the compounds of formula II.

In accordance with another process, these compounds can be prepared from a ketone of general formula:

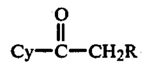

V in which R and Cy have the same meaning as above, either by chloration with chlorine in methylene chloride at 20° C. or in N,N-dimethylformamide at 90°–95° C. or with cupric chloride in N,N-dimethylformamide at 80°–90° C. in accordance with the method described in J. Org. Chem. 28, 630–63 (1963) or by the action of bromine at 20° C. in an appropriate solvent, for instance dioxan or an ethyl ether/dioxan mixture in accordance with the method described in C.A. 97, 162599g (1982) or again with pyridinium tribromide in dioxan.

An excess of chlorine in methylene chloride at 20° C. or in N,N-dimethylformamide at 90°–95° C. or of pyridinium tribromide in dioxan provokes, in some cases, the substitution of the Cy ring by an atom of chlorine or of bromine in addition to the formation of an α-monohalogeno-ketone.

For example, the treatment of 1-(6-methoxy-2-naphthyl)-1-propanone with a chlorinating or brominating agent in excess, as indicated above, leads to the substitution of the naphthyl ring in the 5-position by an atom of chlorine or of bromine and to the formation of 2-chloro-1-(5-chloro-6-methoxy-2-naphthyl)-1-propanone (yield: 87%) or of 2-bromo-1-(5-bromo-6-methoxy-2-naphthyl)-1-propanone.

As mentioned above, the α-hydroxy-alkanoic acids of formula I can be used as intermediate products for the preparation of the alkanoic acids of formula (I') above.

For this purpose, the compounds of formula I will be used following procedures such as:

(a) Dehydration under reflux in a solvent by means, for instance, of p-toluenesulphonic acid followed by catalytic hydrogenation in a solvent of the 2-alkenoic acid obtained, by applying the method described in Patent Application No. 2,613,817 of the Federal Republic of Germany.

(b) Hydrogenolysis of the α-hydroxy-acids, for instance in the presence of RANEY's nickel in acetic acid at 170° C. and under 16 atmospheres as described in Japanese Patent Application No. 53-02449 (C.A. 89, 611 8d) or in the presence of palladium charcoal in acetic acid at 60° C. and under 30 atmospheres as described in Japanese Patent Application No. 53-34745 (C.A. 89, 108684e).

Alterations to the above prior methods can also be made by using either palladium charcoal or sulphuric acid as catalyst and thus operating at atmospheric pressure or by using hydriodic acid in acetic acid.

As mentioned above, the process of the invention has been found to be far superior to the processes suggested by the prior art involving transposition reactions of α,α-dihalogenated ketones.

To this end, trials aimed at the transposition of 2-bromo-1-(4-isobutyl-phenyl)-1-propanone to 2-(4-isobutyl-phenyl)-2-hydroxy-propionic acid were carried out following the process of the invention.

The following results were obtained:

| Reagents and solvent for 1 g of ketone | | | Transposition reaction | | Molar yields (%) | |
|---|---|---|---|---|---|---|
| NaOH (g) | Water (ml) | Xylene (ml) | Temperature | Duration (h) | A* | B** |
| 20 | 400 | 40 | Boiling | 24 h, 7 of which with air bubbling | 78 | 27 |
| 20 | 200 | 40 | Boiling | 24 h with oxygen bubbling | 79 | 18 |

For purposes of comparison, transposition assays were made of an α,α-dihalogenated phenylalkylketone i.e. 2,2-dichloro-1-(4-isobutyl-phenyl-1-propanone to 2-(4-isobutyl-phenyl)-2-hydroxy-propionic acid in accordance with prior art conditions:

| Working conditions | Molar yields (%) A* | B** |
|---|---|---|
| NaOH 20%/water/20° C./29 h | 0 | 7 |
| NaOH 20%/water/60° C./2.5 h + ethanol/1 additional hour | 0 | 33 |
| NaOH 32%/water/20° C./6 h + ethyleneglycol + ethanol/1 h. | 19 | 40 |

*2-(4-isobutyl-phenyl)-2-hydroxy-propionic acid
**4-isobutyl-benzoic acid.

These results show the marked superiority of the process of the invention.

The following non-limitative Examples illustrate the process of the invention:

EXAMPLE 1

Preparation of 2-(4-isobutyl-phenyl)-2-hydroxy-propionic acid (a) 2Bromo-1-(4-isobutyl-phenyl)-1-propanone While stirring, 163 g (1.02 mol) of bromine were added, in 50 min. and at 20°–25° C. to a solution of 184 g (0.97 mole) of 1-(4-isobutyl-phenyl)-1in 150 ml of anhydrous ethyl ether and 37 ml of anhydrous dioxan.

When the operation of introduction was terminated the medium remained coloured. Stirring was maintained for a further 30 min. at 20°–25° C. and then 370 ml of water were added without going beyond 25° C.

After extracting with ethyl ether, the organic phases were washed with saline water, dried on sodium sulphate and heated do dryness under vacuum.

In this manner, 272 g of 2-bromo-1-(4-isobutyl-phenyl)-1-propanone were obtained titrating 89% in gaseous phase chromatography (G.P.C.) corresponding to a molar yield of 92.9%.

An analytical sample was prepared by cristallisation from methanol.

M.P.: 61.4° C.

G.P.C.: 99%

I.R. (film)

1685, 1610 $cm^{-1}$

N.M.R. ($CCl_4$)

7.90 and 7.20 (2d, 4H); 5.20 (q, 1H); 2.55 (d, 2H); 1.85 (d and m, 4H); 0.95 ppm (d, 6H)

| Analysis | | | | |
|---|---|---|---|---|
| C | calculated: | 58.00% | found: | 57.95% |
| H | calculated: | 6.36% | found: | 6.42% |

-continued

| | Analysis | | | |
|---|---|---|---|---|
| Br | calculated: | 29.69% | found: | 30.10% |

(b) 2-(4-Isobutyl-phenyl)-2-hydroxy-propionic acid

Into a 500 ml bomb-apparatus were introduced 2 g ($7.3\times10^{-3}$ mol) of 2-bromo-1-(4-isobutyl-phenyl)-1-propanone (G.P.C.: 98.2%), 7.2 g (0.18 mol) of sodium hydroxide in pellets, 200 ml of water and 40 ml of xylene. The reaction medium was heated to 200° C. and then an air pressure of 20 bars was applied while stirring for 15 min. in these conditions. After cooling to 20° C. and decompression, the medium was decanted and the aqueous phases were re-extracted with ethyl ether. After acidification to pH=1 with concentrated hydrochloric acid, the medium was again extracted with ethyl ether. The last ethereal phases were washed with water, dried on sodium sulphate and heated to dryness under vacuum.

In this manner, 1.45 g of 2-(4-isobutyl-phenyl)-2-hydroxy-propionic acid were obtained titrating 85.2% in G.P.C. namely a yield of 76.2%.

Using the same method as that described above but with the alterations indicated below, 2-(4-isobutyl-phenyl)-2-hydroxy-propionic acid was obtained with the yields given hereunder:

(a) Reaction mixture at 200° C. using an air pressure of 20 bars for 1 hour. Yield: 77%

(b) Reaction mixture at 220° C. using an air pressure of 28 bars for 30 min. Yield: 72%

EXAMPLE 2

Preparation of 2-(4-isobutyl-phenyl)-2-hydroxy-propionic acid (a) 2-Chloro-1-(4-isobutyl-phenyl)1-propanone In 60 ml of dimethylformamide were dissolved 40.9 g (0.24 mol) of dihydrated cupric chloride and 5.09 g (0.12 mol) of lithium chloride. The dissolution was exothermic and the temperature increased to 50° C. The medium was heated to about 80° C. and, in 5 min., 19 g (0.1 mol) of 1-(4-isobutyl-phenyl)-1-propanone were added. The reaction mixture was stirred for 6 hours at 80°-90° C. and then cooled to 20° C. The medium was poured into iced water and acidified to pH=1 with concentrated hydrochloric acid. After extraction with ethyl ether, the organic phases were washed first with acidified water and then with water. After drying on sodium sulphate the medium was heated to dryness under vacuum.

In this manner, 22.3 g of 2-chloro-1-(4-isobutyl-phenyl)-1-propanone were obtained titrating 90.6% in G.P.C. namely a yield of 89.9%.

An analyticial sample was prepared by crystallisation from methanol.

M.P.: 50° C.

G.P.C.: 99.6%

I.R. (film)

1690, 1610 $cm^{-1}$

N.M.R. ($CCl_4$)

7.85 and 7.15 (2 d, 4H); 5.10 (q,1H); 2.50 (d,2H); 2.00 (m,1H); 1.65 (d, 3H);0.90 ppm (d, 6H)

| | Analysis | | | |
|---|---|---|---|---|
| C | calculated: | 69.48% | found: | 69.64% |
| H | calculated: | 7.62% | found: | 7.31% |

-continued

| | Analysis | | | |
|---|---|---|---|---|
| Cl | calculated: | 15.78% | found: | 15.78% |

(b) 2-(4-Isobutyl-phenyl)-2-hydroxy-propionic acid

Proceeding as described in Example 1 there were obtained from 2-chloro-1-(4-isobutyl-phenyl)-1-propanone (G.P.C.: 94.7%), 1.75g of 2-(4-isobutyl-phenyl)-2-hydroxy-propionic acid titrating 78.6% in G.P.C. corresponding to a yield of 74%.

EXAMPLE 3

Preparation of 2-(4-isobutyl-phenyl)-2-hydroxy-acetic acid (a) 2-Bromo-tb 1-(4-isobutyl-phenyl)-ethanone In 15 min. and at 20°-25° C., 33.7 g (0.21 mol) of bromacetyl chloride were added to a suspension of 28 g (0.21 mol) of aluminium chloride in 80 ml of anhydrous methylene chloride.

A beige-coloured suspension was obtained to which 26.9 g (0.2 mol) of isobutylbenzene were added in 10 min. at 20°-25° C.

The reaction mixture was stirred for 4 h 30 min. at 20°-25° C. and then 100 ml of 10%-hydrochloric acid were added, the medium being cooled with an iced water bath to avoid going beyond 25° C.

After washing, the aqueous phase was extracted with methylene chloride. The organic phases were washed with water, dried on sodium sulphate and heated to dryness under vacuum.

In this manner, 50. g of 2-bromo-1-(4-isobutyl-phenyl)-ethanone were obtained titrating 92.2% in G.P.C. namely a yield of 90.4%.

An analytical sample was prepared by crystallisation from hexane.

M.P.: 39° C.

G.P.C.: 97.8%

I.R. (KBr)

1680, 1610 $cm^{-1}$

N.M.R. ($CDCl_3$)

7.80 and 7.15 (2d, 4H); 4.35 (s, 2H); 2.45 (d, 2H); 1.90 (m,1H); 0.90 ppm (d, 6H).

| | Analysis | | | |
|---|---|---|---|---|
| C | calculated: | 56.53% | found: | 56.93% |
| H | calculated: | 5.93% | found: | 6.03% |
| Br | calculated: | 31.26% | found: | 31.00% |

Proceeding as described above but using chloracetyl chloride, 39.9g of 2-chloro-1-(4-isobutyl-phenyl)-ethanone were obtained titrating 95.5% in G.P.C. namely a yield of 90.5%.

An analytical sample was prepared by crystallisation from hexane.

M.P.: 33.4° C.

G.P.C.: 97.5%

I.R. (KBr)

1710, 1690, 1610 $cm^{-1}$

N.M.R. ($CDCl_3$)

7.90 and 7.30 (2d, 4H); 4.70 (s, 2H); 2.55 (d, 2H); 1.90 (m, 1H); 0.95 ppm (d, 6H).

| | Analysis | | | |
|---|---|---|---|---|
| C | calculated: | 68.41% | found: | 68.08% |
| H | calculated: | 7.18% | found: | 7.17% |

-continued

| Analysis | | | | |
|---|---|---|---|---|
| Br | calculated: | 16.83% | found: | 16.73% |

(b) 2-(4-Isobutyl-phenyl)-2-hydroxy-acetic acid (1) Proceeding as described in Example 1 there were obtained from 2-bromo-1-(4-isobutyl-phenyl)-ethanone (G.P.C.: 96.2%), 1.44g of 2-(4-isobutyl-phenyl)-2-hydroxy-acetic acid titrating 75.6% in G.P.C. namely a yield of 69.5%

(2) Using the procedure described in Example 1 there were obtained from 2-chloro-1-(4-isobutyl-phenyl)-ethanone (G.P.C.: 98.2%), 1.59g of 2-(4-isobutyl-phenyl)-2-hydroxy-acetic acid titrating 80% en G.P.C. namely a yield of 65.7%.

EXAMPLE 4

Preparation of 2-(4-isobutyl-phenyl)-2-hydroxy-butanoic acid.

(a) 2-Bromo-1-(4-isobutyl-phenyl)-1-butanone

Proceeding as described in Example 1, there were obtained from 1-(4-isobutyl-phenyl)-1-butanone 14 g of 2-bromo-1-(4-isobutyl-phenyl)-1-butanone titrating 94.6% in G.P.C. corresponding to a yield of 95.7%.

Distillation under vacuum gave the following:

B.P. 157° C. under 3 mm Hg

G.P.C.: 94.4%

I.R. (film)

1680, 1605 $cm^{-1}$

N.M.R. ($CDCl_3$)

7.90 and 7.20 (2d, 4H); 5.05 (t, 1H); 2.50 (d, 2H); 2.10 (m, 3H); 1.05 and 0.90 ppm (t and d, 9H).

$n_D^{22}$: 1.5425

| Analysis | | | | |
|---|---|---|---|---|
| C | calculated: | 59.37% | found: | 59.04% |
| H | calculated: | 6.76% | found: | 6.92% |
| Br | calculated: | 28.21% | found: | 28.26% |

(b) 2-(4-Isobutyl-phenyl)-2-hydroxy-butanoic acid

Proceeding as described in Example 1, there were obtained from 2-bromo-1-(4-isobutyl-phenyl)-1-butanone (G.P.C.: 93.5%) 1.34g of 2-(4-isobutyl-phenyl)-2-hydroxy-butanoic acid titrating 60.9% in G.P.C. namely a yield of 52.6%

EXAMPLE 5

Preparation of 2-(4-isobutyl-phenyl)-2-hydroxy-butanoic acid (a) 2-Chloro-1-(4-isobutyl-phenyl)-1butanone Proceeding as described in Example 2 there were obtained from 1-(4-isobutyl-phenyl)-1-butanone, 10.9g of 2-chloro-1-(4-isobutyl-phenyl)-1-butanone titrating 81.8% in G.P.C. namely a yield of 80.2%.

A purified sample was prepared by chromatography on a silica column with as eluent hexane alone and then hexane containing up to 2% ethyl acetate. B.P.: 111° C. under 1 mm Hg

G.P.C.: 96.3%

I.R. (film)

1690, 1610 $cm^{-1}$

N.M.R. ($CDCl_3$)

7.90 and 7.25 (2d, 4H); 5.05 (t, 1H); 2.50 (d, 2H); 2.00 (m, 3H); 1.05 and 0.90 ppm (t, d, 9H).

$n_D^{22}$: 1.5428

| Analysis | | | | |
|---|---|---|---|---|
| C | calculated: | 70.43% | found: | 70.77% |
| H | calculated: | 8.02% | found: | 8.28% |
| Cl | calculated: | 14.85% | found: | 14.72% |

(b) 2-(4-Isobutyl-phenyl)-2-hydroxy-butanoic acid

Proceeding as described in Example 1 there were obtained from 2-chloro-1-(4-isobutyl-phenyl)-1-butanone (G.P.C.: 93.1%), 1.32g of 2-(4-isobutyl phenyl)-2-hydroxy-butanoic acid titrating 71.1% in G.P.C. namely a yield of 51%.

EXAMPLE 6

Preparation of 2-(4-isobutyl-phenyl)-2-hydroxy-propionic acid

Into a flask were introduced 1 g of 2-bromo-1-(4-isobutyl-phenyl)-1-propanone, 40 g of sodium hydroxide, 400 ml of water and 40 ml of xylene. The mixture was heated to boiling and maintained at this temperature under stirring for 24 hours including 7 hours under air bubbling.

After cooling to 20° C., the medium was decanted and the aqueous phases were extracted with ethyl ether. After acidification to pH=1 with concentrated hydrochloric acid, the mixture was extracted again with ethyl ether . These last ethereal phases were washed with water, dried on sodium sulphate and heated to dryness under vacuum.

In this manner, 0.82g of 2-(4-isobutyl-phenyl)-2-hydroxy-propionic acid was obtained titrating 78% in G.P.C. namely a yield of 78%.

Proceeding in the same manner as that described above but maintaining the reaction mixture at boiling point for 24 h with oxygen bubbling, 0.77 g of 2-(4-isobutyl-phenyl)-2-hydroxy-propionic acid was obtained titrating 84% in G.P.C. namely a yield of 79%.

EXAMPLE 7

Preparation of 2-(4-isobutyl-phenyl)-2-hydroxy-propionic acid

In a 21 stainless-steel bomb-apparatus, equipped with a central mechanical stirrer, were placed 300 ml of water and 28.8 g (0.72 mol) of sodium hydroxide in pellet form. The apparatus was closed and the inner temperature was brought to 180° C. An air-inlet was then connected under a pressure of 20 bars. Under stirring and in 2 hours, a solution of 40 g (0.146 mole) of 2-bromo-1-(4-isobutyl-phenyl)-1-propanone (G.P.C.: 98.24%) in 80 ml of industrial xylene was introduced by means of a pump. Stirring and temperature were maintained for 15 minutes after the operation of introduction was terminated. The apparatus was then cooled in a current of air.

To the reaction mass cooled to 20° C. were added 67 g of sodium chloride and the whole was stirred for one hour and filtered on fritted glass. The precipitate was washed with ethyl acetate and then taken up in 360 ml of water. The suspension so obtained was acidified with 13.4ml of concentrated hydrochloric acid and filtered. After washing of the precipitate so obtained with water and drying at 50° C. under 5 mm Hg, there were isolated 25.5 g of 2-(4-isobutyl-phenyl)-2-hydroxy-propionic acid titrating 95.5% in G.P.C. namely a molar yield of 75.2%.

EXAMPLE 8

Preparation of 2-(4-isobutyl-phenyl)-2-hydroxy-propionic acid (a) 2-Chloro-1-(4-isobutyl-phenyl)-1-propanone In a solution of 150g (0.75 mol) of 1-(4-isobutyl-phenyl)-1-propanone (G.P.C.: 94.7%) in 900 ml of anhydrous methylene chloride,chlorine was bubbled for about 6 h at 20° C.

The reaction medium was then washed with water, dried on sodium sulphate and heated to dryness under vacuum.

In this manner, 173.7g were obtained of 2-chloro-1-(4-isobutyl-phenyl)1-propanone titrating 91.5% in G.P.C. namely a yield of 94.8%.

(b) 2-(4-Isobutyl-phenyl)-2-hydroxy-propionic acid

Proceeding as described in Example 7 there were obtained from 34.2 g of 2-chloro-1-(4-isobutyl-phenyl)-propanone (G.P.C.: 91.5%), 22.4 g of 2-4-isobutyl-phenyl)-2-hydroxy-propionic acid titrating 98% in G.P.C. namely a yield of 68.1%.

EXAMPLE 9

Preparation of 2-hydroxy-2-(6-methoxy-2-naphthyl)-1-propanone (a) 2-Bromo-1-(6-methoxy-2-naphthy)-1-propanone While stirring, 26.88 g ($84\times10^{-3}$ mol) of pyridinium tribromide (M.P.: 132° C.) were added in 10 min. at 25° C. to a solution of 17.22g ($80\times10^{-3}$ mol) of -(16-methoxy-2-naphthyl)-1-propanone in 120 ml of anhydrous dioxan.

The reaction medium was stirred for 2h30 min. at 25° C. and then 400ml of a 3%-sodium hyposulphite solution were added in about 15 min. The formation of an oil was observed which cristallized. The product was filtered out, washed with water and then dried.

In this manner, 23 g of 2-bromo-1-(6-methoxy-2-naphthyl)-1-propanone were obtained titrating 88.6% in G.P.C. namely a molar yield of 86.9%.

An analytical sample was prepared by recristallisation from ethanol .

M.P.: 86.1° C.

G.P.C.: 96.7%

I.R. (KBr)

1675–1660, 1620 $cm^{-1}$

N.M.R. ($CDCl_3$)

8.50–7.00 (m, 6H); 5.40 (q, 1H); 3.90 (s,3H); 1.90 ppm (d, 3H)

| Analysis | | | | |
|---|---|---|---|---|
| C | calculated: | 57.35% | found: | 56.93% |
| H | calculated: | 4.47% | found: | 4.38% |
| Br | calculated: | 27.26% | found: | 27.40% |

(b) 2-Hydroxy-2-(6-methoxy-2-naphthyl)-propanoic acid

Into a 21-stainless-steel bomb-apparatus, equipped with a mechanical stirrer, were introduced 250 ml of water, 9 g ($225\times10^{-3}$ mol) of sodium hydroxide in pellets, 2.5 g ($8.2\times10^{-3}$ mol) of 2-bromo-1-(6-methoxy-2-naphthyl)-1-propanone and 50 ml of xylene.

The apparatus was closed and the inner temperature was brought to 200° C. An inlet of air under a pressure of 20 bars was then connected and the medium was stirred for 15 min. in these conditions. The apparatus was then cooled in a current of air and the medium was extracted with ethyl ether. The aqueous phase was acidified to pH=1 with concentrated hydrochloric acid and again extracted with ethyl ether. These last organic phases were washed with water, dried on sodium sulphate and heated to dryness under vacuum.

In this manner, 1.77 g of 2-hydroxy-2-(6-methoxy-2-naphthyl)-propionic acid was obtained titrating 75.7% in G.P.C. namely a molar yield of 66.4%.

An analytical sample was prepared by recristallisation from a methylene chloride/ethanol mixture.

M.P. : 173° C.

G.P.C.: 99.1%

I.R. (KBr)

3420, 3200–2500, 1735, 1625–1600 $cm^{-1}$

N.M.R. ($CDCl_3$/$DMSOd_6$)

8.00–7.00 (m, 8H); 3.80 (s, 3H); 1.85 ppm (s, 3H)

| Analysis | | | | |
|---|---|---|---|---|
| C | calculated: | 68.28% | found: | 67.78% |
| H | calculated: | 5.73% | found: | 5.67% |

EXAMPLE 10

Preparation of 2-hydroxy-2-(6-methoxy-2-naphthyl)-1-propanone (a) 2-Chloro-1-(6-methoxy-2-naphthyl)-1-propanone To a solution maintained at 80° C. of 15.14 g ($88\times10^{-3}$ mol) of dihydrated cupric chloride and 1.88 g ($44\times10^{-3}$ mol) of lithium chloride in 35 ml of anhydrous dimethylformamide were rapidly added 8 g ($37\times10^{-3}$ mol) of 1-(6-methoxy-2-naphthyl)-1-propanone. The reaction medium was stirred for 2 hours at 80°–90° C. and then poured onto crushed ice and acidified to pH=1 with concentrated hydrochloric acid. After extraction with ethyl ether, the organic phases were washed with saline water, dried on sodium sulphate and heated to dryness under vacuum.

In this manner, 9.37 g of 2-chloro-1-(6-methoxy-2-naphthyl)-1-propanone were obtained titrating 92.4% in G.P.C. namely a molar yield of 94.2%.

An analytical sample was prepared by crystallisation from a hexane/ethyl ether mixture.

M.P.: 74° C.

G.P.C.: 96.9%

I.R. (KBr)

1675, 1615 $cm^{-1}$

N.M.R. ($CDCl_3$)

8.50–7.00 (m, 6H); 5.30 (q, 1H); 3.9 (s, 3H); 1.75 ppm (d, 3H).

| Analysis | | | | |
|---|---|---|---|---|
| C | calculated: | 67.61% | found: | 66.83% |
| H | calculated: | 5.27% | found: | 5.19% |
| Cl | calculated: | 14.25% | found: | 13.95% |

(b) 2-Hydroxy-2-(6-methoxy-2-naphthyl)-propionic acid

Proceeding as described in Example 9, there were obtained from 2 g ($7.6\times10^{-3}$ mol) of 2-chloro-1-(6-methoxy-2-naphthyl)-1-propanone, 1.33 g of 2-hydroxyl- 2-(6-methoxy-2-naphthyl)-propionic acid titrating 77.5% in G.P.C. namely a molar yield of 55.1%.

EXAMPLE 11

Preparation of 2-hydroxy-2-(2-thienyl)-propionic acid (a) 2-Bromo-1-(2-thienyl)-1-propanone To a solution of 20 g ($141\times10^{-3}$ mol) of 2-propionylthiophene in 20 ml of anhydrous dioxan were added, in 75 min. at room-temperature and while stirring, 22.8 g ($142\times10^{-3}$ mol) of bromine. The reaction became exothermic and the medium was stirred for a further 2 hours at room-temperature. After that, 40 ml of water containing sodium hyposulphite was slowly added.

After extraction with ethyl ether, the organic phases were washed with saline water, dried on sodium sulphate and heated to dryness under vacuum.

In this manner, 31.10 g of 2-bromo-1-(2-thienyl)-1-propanone were obtained titrating 89.3% in G.P.C. namely a molar yield of 89.9%.

An analytical sample was prepared by vacuum distillation.

B.P.: 95° C. under 0.7 mm Hg
G.P.C.: 98.0%
$n_D^{20}$: 1.6014
I.R. (film)
3100, 1660 $cm^{-1}$
N.M.R. ($CDCl_3$)
8.00–7.00 (m, 3H); 5.10 (q, 1H); 1.90 ppm (d, 3H)

| Analysis | | | | |
|---|---|---|---|---|
| C | calculated: | 38.37% | found: | 38.29% |
| H | calculated: | 3.22% | found: | 3.22% |
| S | calculated: | 14.63% | found: | 13.94% |
| Br | calculated: | 36.47% | found: | 36.69% |

(b) 2-Hydroxy-2-(2-thienyl)-propionic acid

Using the procedure described in Example 9, there were obtained from 2 g of 2-bromo-1-(2-thienyl)-1-propanone, 1.40 g of 2-hydroxy-2-(2-thienyl)-propionic acid titrating 76.8% in G.P.C. namely a molar yield of 72.7%.

An analytical sample was prepared by chromatography on magnesium trisilicate using a methylene chloride/methanol mixture as eluent and by recrystallisation from toluene.

M.P.: 113° C.
G.P.C.: 98.9%
I.R. (KBr)
3400, 3300–2500, 1720 $cm^{-1}$
N.M.R. ($CDCl_3$/$DMSOd_6$)
9.00–6.00 (m, 5H); 1.70 ppm (s, 3H)

| Analysis | | | | |
|---|---|---|---|---|
| C | calculated: | 48.82% | found: | 49.07% |
| H | calculated: | 4.68% | found: | 4.70% |
| S | calculated: | 18.62% | found: | 18.26% |

EXAMPLE 12

Preparation of 2-hydroxy-2-phenyl-propionic acid (a) 2-Bromo-1-phenyl-1-propanone To a solution of 27.1 g (0.2 mol) of 1-phenyl-1-propanone in a mixture of 22 ml of ethyl ether and 5 ml of anhydrous dioxan were added, in 20 min. at 20° C. while stirring, 33.6 g (0.21 mol) of bromine.

The medium was stirred for a further 60 min. at 20° C. and then 60 ml of water were slowly added without going beyond 25° C. After extraction with ethyl ether, the organic phaseswere washed with water, dried on sodium sulphate and heated to dryness under vacuum.

In this manner, 43.25 g of 2-bromo-1-phenyl-1-propanone were obtained titrating 95.1% in G.P.C. namely a molar yield of 96.5%.

After distillation a product having the following characteristics was obtained:

B.P.: 92° C. under 0.4 mm Hg
G.P.C.: 96.3%
I.R. (film)
1690 $cm^{-1}$
N.M.R. ($CDCl_3$)
7.95 and 7.50 (2m, 5H); 5.25 (q, 1H); 1.85 ppm (d, 3H).

(b) 2-Hydroxy-2-phenyl-propionic acid

Using the method described in Example 9 there were obtained from 2 g of 2-bromo-1-phenyl-1-propanone, 11.2 g of 2-hydroxy-2-phenyl-propionic acid titrating 58.9% in G.P.C. namely a molar yield of 43.9%.

An analytical sample was prepared after recrystallisation from isopropyl ether.

M.P.: 84° C.
G.P.C.: 97.6%
I.R. (KBr)
3480, 3280, about 2900 large; 1710 $cm^{-1}$
N.M.R. ($DMSOd_6$)
7.80–7.20 (m, 7H); 1.75 ppm (s, 3H)

EXAMPLE 13

Preparation of 2-(5-chloro-6-methoxy-2-naphthyl)-2-hydroxy-propionic acid (a) 2-Chloro-1-(5-chloro-6-methoxy-2-naphthyl)-1 propanone Chlorine was bubbled for 2 hours at 90°–95° C. in a solution of 21.4 g (0.1 mol) of 1-(6-methoxy-2-naphthyl)-1propanone (G.P.C.: 100%) in 100 ml of anhydrous N,N-dimethylformmide. The reaction medium was then cooled to 20° C., the chlorine in excess was eliminated with nitrogen and about 100 ml of water and 100 ml of ethyl ether were added. The product which crystallised was filtered out and washed with water and again with ethyl ether.

After recrystallisation from methanol and drying, there were obtained 12 g of 2-chloro-1-(5-chloro-6-methoxy-2-naphthyl)-1-propanone titrating 96.7% in G.P.C. namely a molar yield of 41.0%.

An analytical sample was prepared by recrystallisation from methanol.

M.P.: 133° C.
G.P.C.: 96.7%
Chlorine: calculated: 25.04%
found 25.16%
I.R. (KBr): 1675, 1620 $cm^{-1}$
N.M.R. ($CDCl_3$)
8.40–7.10 (m, 5H); 5.35 (q, 1H); 3.95 (s, 3H); 1.75 ppm (d, 3H)

| Analysis | | | | |
|---|---|---|---|---|
| C | calculated: | 59.39% | found: | 59.64% |
| H | calculated: | 4.27% | found: | 4.23% |
| Cl | calculated: | 25.04% | found: | 25.11% |

(b) 2-(5-Chloro-6-methoxy-2-naphthyl)-2-hydroxy-propionic acid

Proceeding as described in Example 9 but from 200 ml of water, 7.2 g ($180\times10^{-3}$ mol) of sodium hydroxide in pellets, 2 g ($6.83\times10^{-3}$ mol) of 2-chloro-1-(5-chloro-6-metheoxy-2-naphthyl)-1-propanone (G.P.C.: 96.7%) and 40 ml of xylene, there were obtained 1.5 g of 2-(5- chloro-6-methoxy-2-naphthyl)-2-hydroxy-propionic acid titrating 55% in G.P.C. namely a molar yield of 43.4%.

After recrystallisation from chloroform, a product having the following characteristics was obtained:

M.P.: about 208° C.

G.P.C.: 92.0%

Acidimetric titration: 96.4%

I.R. (KBr)

3400, about 2920 (large), 1715, 1600 $cm^{-1}$

N.M.R. ($CDCl_3$)

8.30–7.35 (m, 7H); 4.00 (s, 3H); 1.9 ppm (s, 3H)

The following Examples illustrate the preparation of alkanoic acids of formula (I') from α-hydroxy-acids of formula I.

EXAMPLE I

Preparation of 2-(4-isobutyl-phenyl)-propionic acid from the corresponding compounds of formula I.

(a) 2-(4-Isobutyl-phenyl)-propenoic acid

A solution of 2.22 g ($9.7\times10^{-3}$ mol) of 2-(4-isobutyl-phenyl)-2-hydroxypropionic acid (G.P.C.: 96.9%) and 2.22 g of monohydrated p-toluenesulphonic acid in 90 ml of benzene was stirred for 2 hours under reflux, the water being eliminated by azeotropy.

After cooling to 20° C., the medium was washed with saline water, dried on sodium sulphate and heated to dryness under vacuum.

In this manner, 1.98g of 2-(4-isobutyl-phenyl)-propenoic acid were obtained titrating 98.8% in G.P.C. namely a molar yield of 99.0%.

An analytical sample was prepared by recrystallisation from hexane.

M.P.: 95° C.

G.P.C.: 100%

I.R.(KBr)

3300–2500, 1670, 1615–1605, 840 $cm^{-1}$

N.M.R. ($CDCl_3$)

11.9 (s, 17.2 (m, 4H); 6.5 and 5.95 (2s, 2×2.45 (d, 2H); about 1.8 (m, 1H); 0.9 ppm (d, 6H).

| Analysis | | | | |
|---|---|---|---|---|
| C | calculated: | 76.44% | found: | 76.27% |
| H | calculated: | 7.90% | found: | 7.88% |

Using the above procedure, 2-(4-isobutyl-phenyl)-2-butenoic acid was obtained from 2-(4-isobutyl-phenyl)-2-hydroxy-butanoic acid in a molar yield of 91.9%.

An analytical sample was prepared by recristallisation from hexane.

M.P.: 47° C.

G.P.C.: 96.4%

I.R.

About 3000 $cm^{-1}$, 1695 $cm^{-1}$

N.M.R. ($CDCl_3$)

12.3 (s, 1H); 7.3–6.95 (m, 4H); 6.35 (q, 1H); 2.45 (d, 2H); 2.1 (d, 2H); 1.9 (m, 1H); 0.9 ppm (d, 6H).

| Analysis | | | | |
|---|---|---|---|---|
| C | calculated: | 77.03% | found: | 76.67% |
| H | calculated: | 8.31% | found: | 8.27% |

(b) 2-(4-Isobutyl-phenyl)-propionic acid

A suspension of 0.80 g ($3.9\times10^{-3}$ mol) of 2-(4-isobutyl-phenyl)-propenoic acid and 40 mg of 5%-palladium charcoal in 16 ml of ethanol was stirred under hydrogen atmosphere for 1.25h at 20° C.

After filtration of the catalyst, the reaction medium was brought to dryness under vacuum.

In this manner, 0.80 g of 2-(4-isobutyl-phenyl)-propionic acid or ibuprofen was obtained titrating 98.1% in G.P.C. namely a molar yield of 97.1%.

M.P.: 78° C.

I.R.

About 3000, 1710 $cm^{-1}$

N.M.R. ($CDCl_3$)

9.95 (s, 1H); 7.1 (m, 4H); 3.65 (q, 1H); 2.45 (d, 2H); 1.95 (m, 1H); 1.45 (d, 3H); 0.9 ppm (d, 6H).

Using the procedure hereabove described, 2-(4-isobutyl-phenyl)-butanoic acid or butibufen was obtained from 2-(4-isobutyl-phenyl)-2-butenoic acid in a yield of 100%.

I.R.

About 3000, 1705 $cm^{-1}$

N.M.R. ($CDCl_3$)

11.25 (s, 1H); 7.1 (m, 4H); 3.4 (t, 1H); 2.45 (d, 2H); 2.2–1.5 (m, 3H); 0.9 ppm (d+t, 9H).

| Analysis | | | | |
|---|---|---|---|---|
| C | calculated: | 76.33% | found: | 76.28% |
| H | calculated: | 9.15% | found: | 9.30% |

EXAMPLE II

Preparation of 2-(4-isobutyl-phenyl)-propionic acid from the corresponding compound of formula I A suspension of 2.22 g ($9.7\times10^{-3}$ mol) of 2-(4-isobutyl-phenyl)-2-hydroxy-propionic acid (G.P.C.: 96.9%), 0.44 g of 5%-palladium charcoal in 20 ml of acetic acid and 2.2 ml of sulphuric acid was stirred under hydrogen atmosphere for 29 hours at 20° C. The reaction medium was filtered and water was added.

After extraction with ethyl ether, the organic phases were washed with water, dried on sodium sulphate and heated to dryness under vacuum.

In this manner, 2.05 g of 2-(4-isobutyl-phenyl)-propionic acid or ibuprofen were obtained titrating 88% in G.P.C. namely a molar yield of 90.4%.

(a) Using the method described above, 2-(4-isobutyl-phenyl)-acetic acid or ibufenac was obtained from 2-(4-isobutyl-phenyl)-2-hydroxy-acetic acid, with a molar yield of 95.3%.

An analytical sample was prepared by recrystallisation from hexane.

M.P.: 85° C.

G.P.C.: 99.7%

I.R. (KBr)

3500–2500, 1695 $cm^{-1}$

N.M.R. ($CDCl_3$)

11.95 (s, 1H); 7.1 (m, 4H); 3.6 (s, 2H); 2.45 (d, 2H); 1.95 (m, 1H); 0.9 ppm (d, 6H).

| Analysis | | | | |
|---|---|---|---|---|
| C | calculated: | 74.97% | found: | 75.38% |
| H | calculated: | 8.39% | found: | 8.47% |

(b) Using the above procedure but starting with 2-(4-isobutyl-phenyl)-2-hydroxy-butanoic acid, 2-(4-isobutyl-phenyl)-butanoic acid or butibufen was obtained with a molar yield of 83.1%.

EXAMPLE III

Preparation of 2-(4-isobutyl-phenyl)-propionic acid from the corresponding compound of formula I.

A solution of 2.22g ($9.7\times10^{-3}$ mol) of 2-(4-isobutyl-phenyl)-2-hydroxypropionic acid (G.P.C.: 96.9 90) in 13 ml of acetic acid and 4.4 ml of 57% hydriodic acid was stirred for 6 hours at 60° C.

The reaction medium was cooled to 20° C. and poured into a sodium hyposulphite solution. After extraction with ethyl ether, the organic phases were washed with water containing sodium chloride, dried on sodium sulphate and brought to dryness under vacuum.

In this manner, 2.06 g of 2-(4-isobutyl-phenyl)-propionic acid titrating 91% in G.P.C. namely a yield of 93.9% were obtained.

EXAMPLE IV

Preparation of 2-(6-methoxy-2-naphthyl)-propionic acid

A mixture of 0.3g ($1.2\times10^{-3}$ mol) of 2-hydroxy-2-(6-methoxy-2-naphthyl)-propionic acid, 1.8ml of acetic acid and 0.6 ml of 57% hydriodic acid was stirred for 3 hours at 60° C. The reaction medium was cooled to 20° C. and poured into an aqueous solution of sodium hyposulphite. The precipitate formed was suction-filtered, washed with water and dried under vacuum at 20° C.

In this manner, 0.268 g of 2-(6-methoxy-2-naphthyl)-propionic acid or naproxen in DL-form was obtained titrating 97.9% in G.P.C. namely a molar yield of 95%.

M.P.: 115.4° C.

G.P.C.: 97.9%

I.R. (KBr)

about 3000, 1710, 1610 $cm^{-1}$

N.M.R. ($CDCl_3$)

11.40 (s, 1H); 7.75–7.05 (m, 6H); 3.85 (s, 3H); 1.55 ppm (d, 3H).

EXAMPLE V

Preparation of 2-(6-methoxy-2-taphthyl)-propionic acid.

(a) 2-(6-Methoxy-2-naphthyl)-propenoic acid.

A mixture of 1.15g ($4.62\times10^{-3}$ mol) of 2-hydroxy-2-(6-methoxy-2-naphthyl)-propionic acid, 0.120 g of p-toluenesulphonic acid, 0.005g of monomethyl hydroquinone in 22 ml of benzene was stirred under reflux, with elimination of water, for 4h.

After cooling to 20° C., the reaction medium was filtered and brought to dryness under vacuum.

After crysrallisation from benzene, there was obtained 0.610 g of 2-(6-methoxy-2-naphthyl)-propenoic acid titrating 87.8% in G.P.C. namely a molar yield of 59.1%.

An analytical sample was prepared after washing with water and recrystallisation from a hexane/ethyl ether mixture.

M.P.: 175° C.

Acidimetric titration: 98.7%

I.R. (KBr)

about 2950 large, 1685, 1635, 1605 $cm^{-1}$

N.M.R. ($CDCl_3+DMSOd_6$)

7.90–6.90 (m, 7H); 6.35 and 5.99 (2s, 1H); 3.85 ppm (s, 3H).

| Analysis | | | | |
|---|---|---|---|---|
| C | calculated: | 73.67% | found: | 73.60% |
| H | calculated: | 5.30% | found: | 5.34% |

(b) 2-(6-Methoxy-2-naphthyl)-propionic acid

Using the method described in Example 1 b) 2-(6-methoxy-2-naphthyl)-propionic acid or naproxen in DL-form was obtained from 2-(6-methoxy-2-naphthyl)-propenoic acid.

EXAMPLE VI

Preparation of 2-(6-methoxy-2-naphthyl)-propionic acid

A solution of 2 g ($7.3\times10^{-3}$ mol) of 2-hydroxy-2-(6-methoxy-2-naphthyl)-propionic acid and 0.2 g or p-toluenesulphonic acid in 50 ml of dichlorethane was stirred under reflux, with elimination of water, for 16h30 min.

After cooling to 20° C., 0.1 g of 5% -palladium charcoal was added and after the usual draining, the medium was stirred under hydrogen atmosphere for 6 hours at 20° C. The catalyst was filtered out with caution and the organic phases were brought to dryness under vacuum.

In this manner, 2-(6-methoxy-2-naphthyl)-propionic acid in crude form or naproxen in DL-form was obtained with a yield of 48.9%.

EXAMPLE VII

Preparation of 2-(2-thienyl)-propionic acid

Using the same procedure as that described in Example IV, 0.50 g of 2-(2-thienyl)-propionic acid titrating 98.1% in G.P.C. was obtained from 0.60 g ($3.3\times10^{-3}$ mol) of 2-hydroxy-2-(2-thienyl)-propionic acid namely a molar yield of 95.3%.

An analytical sample was prepared by passing through a column of magnesium trisilicate using a methylene chloride/methanol mixture as eluent.

G.P.C.: 98.

N.M.R.:($CDCl_3$)

10.10 (s, 1H); 7.30–6.80 (m, 3H); 4.00 (q, 1H); 1.55 ppm (d, 3H).

We claim:

1. A process for preparing α-hydroxy-acids of general formula:

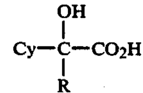

I in which R represents a lower alkyl radical and Cy represents a phenyl, naphthyl or thienyl radical, these latter three radicals optionally comprising one or more substituents selected from the group consisting of lower alkyl, lower alkenyl, lower alkynyl, lower alkoxy radicals and halogen atoms wherein: an α-monohalogenated ketone of general formula:

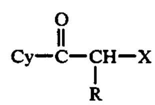

II in which R and Cy have the same meaning as above and X represents chlorine, bromine or iodine is treated, in the presence of an aqueous solution of an alkali metal hydroxide, a non-polar organic solvent selected from an aromatic or alicyclic hydrocarbon and oxygen in excess optionally in the presence of an inert gas, the treatment being carried out at a temperature ranging from the boiling temperature of the reaction medium at atmospheric pressure and 240° C. under pressure, and the alkali metal salt so formed is acidified to obtain the desired acid.

2. A process according to claim 1 wherein the alkali metal hydroxide is lithium, sodium or potassium hydroxide.

3. A process according to claim 1 wherein the aromatic hydrocarbon is xylene.

4. A process according to claim 1 wherein R represents methyl or ethyl.

5. A process according to claim 1 wherein Cy represents a 4-isobutyl-phenyl radical.

6. A process according to claim 1 wherein Cy represents a 6-methoxy-2-naphthyl radical.

7. A process according to claim 1 wherein Cy represents a 2-thienyl radical.

8. A process according to claim 1 wherein:

0.5 to 40 parts by weight of alkali metal hydroxide, 5 to 400 parts by volume of water, and 2 to 40 parts by volume of organic solvent, are used for 1 part by weight of α-monohalogenated ketone, the treatment being carried out at the boiling temperature of the reaction medium at atmospheric pressure.

9. A process according to claim 1 wherein:

0.5 to 10 parts by weight of alkali metal hydroxide, 5 to 150 parts by volume of water, and 1 to 30 parts by volume of organic solvent, are used for 1 part by weight of α-monohalogenated ketone, the treatment being carried out at a temperature ranging from the boiling temperature of the reaction medium at atmospheric pressure and 240° C. under pressure.

10. A process according to claim 1 wherein the treatment is carried out at a temperature of 180 ° to 220° C.

11. A process according to claim 1 wherein the treatment is carried out in a bomb-apparatus at a temperature ranging from the boiling temperature of the reaction medium at atmospheric pressure and 240° C. by introducing, in a continòus manner, the α-monohalogenated ketone into the said reaction medium.

12. A process according to claim 1 wherein oxygen in the presence of an inert gas is represented by air.

13. A process according to claim 1 werein the alkali metal hydroxide is lithium, sodium or potassium hydroxide, R represents methyl or ethyl, and Cy represents a 4-isobutyl-phenyl, a 6-methoxy-2-naphthyl or a 2-thienyl radical.

14. A process according to claim 13 wherein the aromatic hydrocarbon is xylene.

15. A process according to claim 8 wherein the alkali metal hydroxide is lithium, sodium or potassium hydroxide, R represents methyl or ethyl, and Cy represent a 4-isobutyl-phenyl, 6-methoxy-2-naphthyl or 2-thienyl radical.

16. A process according to claim 15 wherein the aromatic hydrocarbon is xylene.

17. A process according to claim 9 wherein the alkali metal hydroxide is lithium, sodium or potassium hydroxide, R represents methyl or ethyl, and Cy represents a 4-isobutyl-phenyl, a 6-methoxy-2-naphthyl or a 2-thienyl radical.

18. A process according to claim 17 wherein the aromatic hydrocarbon is xylene.

* * * * *

UNITED STATES PATENT AND TRADEMARK OFFICE

CERTIFICATE OF CORRECTION

PATENT NO. : 4,675,419

DATED : June 23, 1987

INVENTOR(S) : ANDRE et al

It is certified that error appears in the above-identified patent and that said Letters Patent is hereby corrected as shown below:

On the cover page, the Assignee should be listed as --SANOFI, Paris, France, and INDUSTRIA CHIMICA PRODOTTI FRANCIS S.p.A., Caronno P.lla, Italy--

Signed and Sealed this

Sixteenth Day of August, 1988

*Attest:*

DONALD J. QUIGG

*Attesting Officer*

*Commissioner of Patents and Trademarks*